US00PP33630P2

(12) United States Plant Patent
Hansen

(10) Patent No.: US PP33,630 P2
(45) Date of Patent: Nov. 9, 2021

(54) **X *MANGAVE* PLANT NAMED 'CENTER OF ATTENTION'**

(50) Latin Name: **x *Mangave* hybrid**
Varietal Denomination: Center of Attention

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 16 days.

(21) Appl. No.: 16/873,809

(22) Filed: Jul. 14, 2020

(51) Int. Cl.
*A01H 5/12* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 5/12
See application file for complete search history.

*Primary Examiner* — Kent L Bell

(57) ABSTRACT

A new and unique x *Mangave* plant named 'Center of Attention' characterized by a short, rounded mound of fleshy, linear to lanceolate leaves that are flat and mostly straight with light greyed green to greyed-purple and a central band of burgundy-red, margins develop glaucous, dark greyed-purple spotting with intense light. The leaves have numerous medium-sized, firm but flexible marginal teeth distally pointing outwardly and pointing backward in proximal region. Flowers are yellowish and clustered in terminal branches of erect scapes. The new plant is suitable for the garden or as a potted plant in the garden or home.

2 Drawing Sheets

Botanical classification: x *Mangave* hybrid.
Variety denomination: 'Center of Attention'.

STATEMENT REGARDING PRIOR DISCLOSURES UNDER 37 CFR 1.77(B)(6)

The first public disclosures of the claimed plant, in the form of private sales, were made by Walters Gardens, Inc. on Oct. 22, 2019 to Plant Delights Nursery, Inc. followed by a sale to San Marcos Growers on Nov. 11, 2019. Plants for these sales were obtained from the inventor. Subsequently, on Mar. 3, 2020, Walters Gardens, Inc. posted on their website a non-enabling photograph with brief description. Information for this website was obtained from the inventor. No plants of x *Mangave* 'Center of Attention' have been sold, in this country or anywhere in the world nor has any disclosure of the new plant been made more than one year prior the filing date of this application, and such sale or disclosure within one year was obtained either derived directly or indirectly from the inventor.

BACKGROUND OF THE INVENTION

The present invention relates to the new and distinct x *Mangave* hybrid plant, x *Mangave* 'Center of Attention' that was hybridized by the inventor at a wholesale perennial nursery in Zeeland, Mich., USA as a cross between a proprietary selection of *Agave nizandensis* (not patented) as the female or seed parent times and an unreleased proprietary hybrid known as 12-3-31 (not patented) as the male or pollen parent. The cross was performed Jun. 27, 2015 and seeds were harvested and sown in the autumn of 2015. Through trials at the same nursery the plant was assigned the breeder code 15-194-6. The new plant has been successfully asexually propagated by sterile shoot-tip tissue culture and by basal offsets at the same nursery in Zeeland, Mich. The asexual tissue culture propagation has been found to produce stable and identical plants that maintain all the unique characteristics of the original plant in successive generations.

BRIEF SUMMARY OF THE INVENTION

'Center of Attention' differs from its parents as well as all other *Manfreda, Agave* and x *Mangave* known to the applicant. The female parent has fewer leaves per plant, narrower leaves with medium-green on the margins and lighter green in the center and lacks the dark greyed-purple spotting and the glaucous surfaces. The male parent has more wavy, wider leaves with larger teeth and the habit is more upright with more leaves per plant. The nearest comparison plants are: 'Blazing Saddles' U.S. Plant Pat. No. 31,274, 'Desert Dragon' U.S. Plant Pat. No. 31,311, 'Painted Desert' U.S. Plant Pat. No. 31,630 and 'Racing Stripes' U.S. Plant Pat. No. 31,251. 'Blazing Saddles' has shorter and narrower leaves that produce larger spots of less dense reddish to greyed reddish-purple spotting with more green background and lacks the lighter midrib, and the foliage has less glaucous surface. 'Desert Dragon' has foliage that is more folded and sinuate and the center midrib lacks the reddish purple coloration. 'Painted Desert' has less arching and more upright habit with flatter and narrower leaves that have smaller teeth and the center midrib is more chartreuse. 'Racing Stripes' has narrower leaves that are more green with lighter green midrib, firmer cinnamon-colored teeth, and more spotting on the foliage.

'Center of Attention' is unique from all of the above cultivars and all *Agave*, x *Mangave* and *Manfreda* known to the inventor by the following combined traits:

1. Medium, linear to lanceolate, flat, mostly straight, sarcous leaves;

2. Leaves develop large, dense, dark greyed-purple spotting on a glaucous, light greyed- green to greyed-purple background, and a central band of burgundy-red;
3. Leaf margins have many, medium-sized, flexible, mostly outwardly-facing, marginal teeth;
4. Moderate growth rate;

BRIEF DESCRIPTION OF THE DRAWING

The photographs of x *Mangave* 'Center of Attention' demonstrate the overall appearance of the new plant including the unique traits as a two-year-old plant grown in a greenhouse and moved to a full-sun trial garden in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
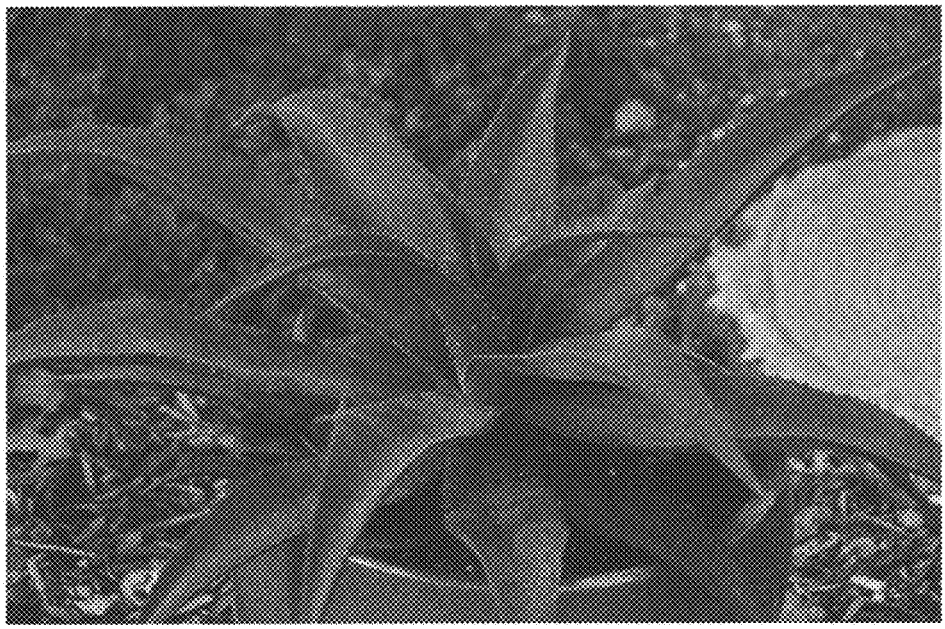
FIG. 1 shows the new plant from the side angle.
Figure 2:
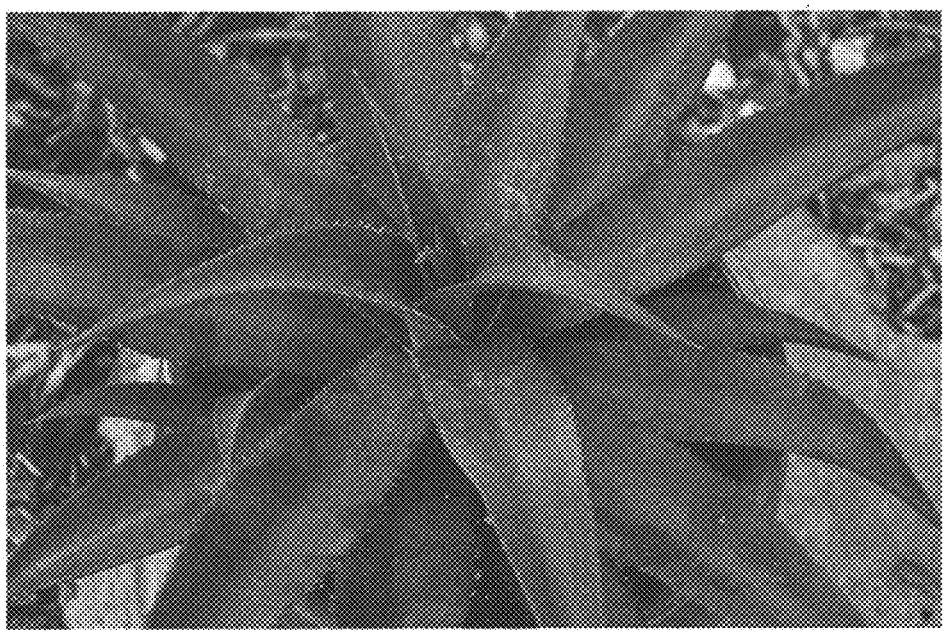
FIG. 2 shows a view from above.
Figure 3:
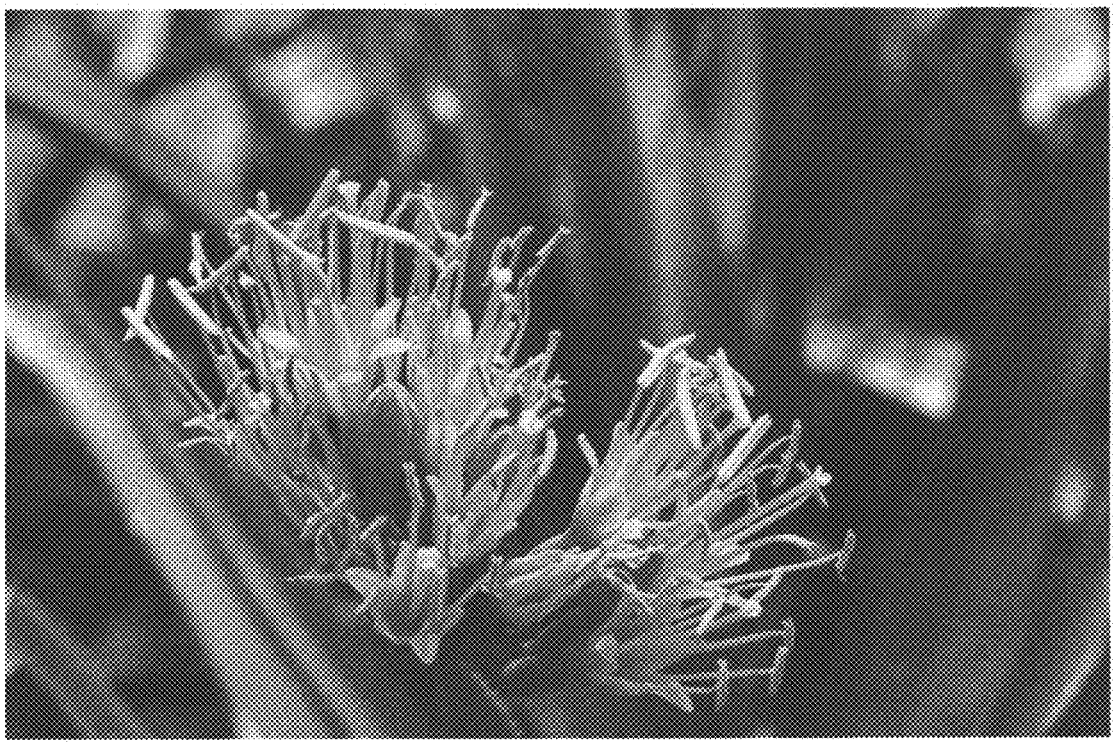
FIG. 3 shows a close-up of the flowers and buds.

The following descriptions and color references are based on the 2015 edition of The Royal Horticultural Society Colour Chart except where common dictionary terms are used. The new plant, x *Mangave* 'Center of Attention', has not been observed under all possible environments. The phenotype may vary slightly with different environmental conditions, such as temperature, light, fertility, moisture and maturity levels, but without any change in the genotype. The following observations and size descriptions are of a three-year-old plant in a commercial wholesale greenhouse in Zeeland, Mich. with supplemental water and fertilizer as needed.

Parentage: A proprietary unnamed selection of *Agave nizandensis* as the female or seed patent, an unreleased proprietary hybrid known as 12-3-31 (*Mangave* 'Bloodspot' (not patented) x a proprietary selection of *Agave gypsophila* (not patented)) as the male or pollen parent;

Propagation: By sterile shoot-tip tissue culture;

Time to initiate roots from tissue culture: About 21 days;

Growth rate: Moderate;

Crop time: About 14 to 18 weeks to finish in a 3.8 liter container from a 35 mm tissue culture growing at about 21° C.;

Rooting habit: Fleshy, lightly branching, with roots up to 30 cm long;

Root color: Nearest RHS 158B;

Plant shape and habit: Succulent herbaceous perennial with basal rosettes of about 64 leaves radially emerging, stiff, mostly straight from central stem, producing a radially-symmetrical, rounded mound;

Plant size: Foliage height about 30.0 cm tall from soil line to the top of the leaves and about 76.0 cm wide at the widest point just above soil level;

Stem: To about 3.5 cm across; covered with foliage;

Foliage description: Linear to lanceolate; simple; sessile; bi-laterally symmetrical; sarcous; apex narrowly acute with terminal mucro; base truncate; older lower leaves becoming flat; mostly outwardly pointing teeth curving backward in proximal portion; both adaxial and abaxial glabrous and heavily glaucous;

Mucro (apical spine): About 8.0 mm long and 1.5 mm wide; flexible;

Marginal teeth: Medium size, firm, but flexible even when mature; protruding about 2.0 mm long from margin and 2.0 mm wide at base, average spacing about 5.0 mm apart;

Leaf size: To about 38.6 cm long, about 66.0 mm wide toward middle; center base about 12.0 mm thick at basal midrib; average about 36.5 cm long, 57.0 mm wide and 12.0 mm thick in longitudinal center; spotted to blushed with greyed-purple near stem on both adaxial and abaxial;

Foliage fragrance: None observed;

Leaf number: About 64 per plant before flowering;

Leaf blade color:

*Adaxial* (*low light*).—Young and mature leaves nearest RHS 137A along margins, and between RHS 146B and RHS 146C along center midrib, with spots on margin and center nearest a blend of N187B and RHS 186B.

*Abaxial* (*low light*).—Young and mature leaves margin and center nearest RHS 144A, with occasional spots of nearest a blend of N186B and RHS N186C and leaf base of nearest blend between RHS N187B, RHS 187D and RHS 186D.

*Adaxial* (*high light*).—Young and mature leaf margins a blend between N186A and RHS N187A with an occasional small spot about 2.0 mm diameter of nearest RHS 137A, midrib distally nearest RHS N77B; center nearest a blend between RHS N187C and RHS N77B.

*Abaxial* (*high light*).—Young and mature leaf margins and center a blend between N186A and RHS N187A with an occasional small spot about 2.0 mm diameter of nearest RHS 137A, midrib distally nearest RHS N77B.

*Teeth*.—On young leaves adaxial and abaxial nearest RHS 145A, mature leaves adaxial and abaxial nearest RHS NN155C toward apex and base nearest RHS N186A.

*Mucro*.—Nearest RHS N200B.

Petiole: Leaves sessile;

Veins: Parallel; not distinct abaxial or adaxial;

Peduncle: Terete; glaucous; glabrous; stiff; strong; lightly branched; about 170 cm long and 28 mm diameter at base and 18.0 mm diameter below first flowers; flowering portion about 87 cm tall and about 45 cm across; branches to about 28 cm long and about 4 mm diameter at base; attitude main peduncle erect and branches upward and outwardly;

Peduncle color: Basal portion before flowers nearest a blend between RHS N186C and RHS 147A, flowering portion nearest a blend between RHS 138A and RHS 147A;

Pedicel: Terete; glaucous; glabrous; stiff; strong; average about 2.5 mm long and 2.2 mm diameter;

Pedicel color: Nearest RHS 138A;

Cauline leaves: About 17 per scape; lanceolate; simple, fleshy, glabrous; margins finely dentate with flexible teeth; apex narrowly acute with flexible mucro; base truncate, sessile, clasping; proximally about 14 cm long and about 18 mm wide at base, decreasing distally; color adaxial and abaxial nearest RHS N77B;

Buds one day prior to opening: Elongated globose; about 3.8 cm long and about 11.0 mm across at mid-tepal, base about 4.0 mm diameter;

Bud color: Nearest RHS 138A in basal portion and distally becoming nearest RHS 162A;

Flower description: Perfect, actinomorphic; about 6.5 cm long and opening to about 30 mm across at outside of anthers; lasting about 3 to 4 days per flower; flowering period about three weeks in late winter in Michigan greenhouse; producing abundant nectar; forming in clusters near distal ends of branches; approximately 200 flowers per scape; attitude mostly upright;

Flower fragrance: Not detected;

Tepals: Six in two sets of three; glaucous abaxial and slightly lustrous adaxial; glabrous both adaxial and abaxial; acute apex and fused base; outer set about 4.8 cm long, separated in the distal 16 mm, fused in basal 3.2 cm, about 6.0 mm wide at base; inner set about 4.8 cm long, separated in distal 16 mm, fused in basal 3.2 cm, and 7.0 mm wide at fusion; inner set creased along edge where overlapped with outer set while in bud;

Tepal color: Adaxial outer and inner tepal set base and distal portion nearest RHS 138A; abaxial outer set base nearest RHS 138A with distal non-fused portion nearest RHS 16A, abaxial inner set base nearest RHS 138A, margin nearest RHS 16A and center nearest RHS 151B; inner and outer sets becoming nearest RHS 21A distally with age adaxial and abaxial;

Androecium: Six;

*Filaments*.—Six; terete distally, slightly applanate base; stiff and straight; about 4.6 cm long and 1.0 mm diameter at base; color nearest RHS 1C.

*Anther*.—Dorsifixed; longitudinal; about 1.6 cm long and 2.0 mm diameter before opening; after dehiscence remaining straight; color nearest RHS 4C.

*Pollen*.—Abundant; color nearest RHS 16A.

Gynoecium: Single;

*Style*.—6.4 cm long and 2.0 mm diameter at base; color nearest RHS 4B.

*Stigma*.—Turbinate, apex tri-lobed; about 2.5 mm tall and 3.5 mm across top; color side nearest RHS 4D; top stigmatic surface in tri-pointed star with color nearest RHS 4D.

*Ovary*.—Inferior.

Fruit and seed: Not yet observed;

Disease resistance: x *Mangave* 'Center of Attention' has not been observed to be resistant or susceptible to diseases beyond that which is normal for x *Mangave, Agave* or *Manfreda*. The new plant is xeromorphic and survives well with minimal water once established. The new plant is estimated to be winter hardy at least to USDA zone 9. Full extent of winter hardiness has not been tested.

It is claimed:

1. A new and distinct cultivar of ornamental x *Mangave* plant named 'Center of Attention' as herein described and illustrated.

* * * * *